US012685650B2

(12) United States Patent
Schultz et al.

(10) Patent No.: US 12,685,650 B2
(45) Date of Patent: Jul. 21, 2026

(54) TOOL FOR ASSEMBLING AND DISASSEMBLING IMPLANT COMPONENTS

(71) Applicant: WALDEMAR LINK GMBH & CO. KG, Hamburg (DE)

(72) Inventors: Thomas Schultz, Adendorf (DE); Alexander Etringer, Bremen (DE); Paolo Dalla Pria, Udine (IT)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 291 days.

(21) Appl. No.: 18/556,751

(22) PCT Filed: Apr. 23, 2022

(86) PCT No.: PCT/EP2022/060790
§ 371 (c)(1),
(2) Date: Oct. 23, 2023

(87) PCT Pub. No.: WO2022/229039
PCT Pub. Date: Nov. 3, 2022

(65) Prior Publication Data
US 2024/0197497 A1     Jun. 20, 2024

(30) Foreign Application Priority Data
Apr. 26, 2021    (EP) ..................................... 21170401

(51) Int. Cl.
*A61F 2/46*        (2006.01)
*A61F 2/30*        (2006.01)

(52) U.S. Cl.
CPC .. *A61F 2/4637* (2013.01); *A61F 2002/30332* (2013.01); *A61F 2002/30433* (2013.01);
(Continued)

(58) Field of Classification Search
CPC .................. A61F 2/4603; A61F 2/4637; A61F 2002/4619; A61F 2002/4622;
(Continued)

(56) References Cited

U.S. PATENT DOCUMENTS 5,413,603 A * 5/1995 Noiles ................. A61F 2/30721
623/23.43
5,417,693 A   5/1995 Sowden et al.
(Continued)

FOREIGN PATENT DOCUMENTS

DE           7601139 U1     5/1976

OTHER PUBLICATIONS

International Search Report and Written Opinion mailed Jul. 29, 2022, in connection with International Patent Application No. PCT/EP2022/060790, 12 pgs.
(Continued)

*Primary Examiner* — Anu Ramana
(74) *Attorney, Agent, or Firm* — Chiesa Shahinian & Giantomasi PC

(57)          ABSTRACT
The present disclosure discloses a tool for assembling and disassembling a first implant component and a second implant component. The tool comprises a proximal end, a distal end, and a longitudinal axis and further includes an elongated force transmission structure for transmitting a force in a direction along the longitudinal axis, the force transmission structure configured to attach to an assembly adapter or a disassembly adapter; two elongated retaining elements, each retaining element having a distally facing retaining surface at a proximal end thereof; and an actuation mechanism, wherein the actuation mechanism is operable to move the retaining elements between a standby position and a retaining position.

13 Claims, 3 Drawing Sheets

(52) U.S. Cl.
CPC ................. *A61F 2002/4622* (2013.01); *A61F 2002/4627* (2013.01); *A61F 2002/4628* (2013.01); *A61F 2002/4638* (2013.01); *A61F 2002/4641* (2013.01)

(58) Field of Classification Search
CPC ...... A61F 2002/4625; A61F 2002/4627; A61F 2002/4628; A61F 2002/4638; A61F 2002/4641; A61F 2/4607
See application file for complete search history.

(56) References Cited

U.S. PATENT DOCUMENTS

| | | | | |
|---|---|---|---|---|
| 6,488,713 | B1 * | 12/2002 | Hershberger | ....... A61F 2/30744 |
| | | | | 623/18.11 |
| 6,613,093 | B2 * | 9/2003 | DeCarlo, Jr. | ......... A61F 2/3662 |
| | | | | 623/23.26 |
| 7,879,042 | B2 * | 2/2011 | Long | ..................... A61F 2/4609 |
| | | | | 623/22.12 |
| 8,162,947 | B2 * | 4/2012 | Dreyfuss | ............... A61F 2/3877 |
| | | | | 606/86 R |
| 8,535,324 | B2 * | 9/2013 | Aux Epaules | ........ A61F 2/4609 |
| | | | | 606/88 |
| 8,840,622 | B1 | 9/2014 | Vellido et al. | |
| 9,089,440 | B2 * | 7/2015 | Mueller | .................. A61F 2/461 |
| 9,125,744 | B2 * | 9/2015 | Gradel | .................. A61F 2/4609 |
| 9,375,316 | B2 * | 6/2016 | Meridew | ............. A61F 2/30724 |
| 10,772,739 | B2 * | 9/2020 | Sweitzer | ............... A61F 2/4609 |
| 11,413,152 | B2 * | 8/2022 | Albert | ................... A61F 2/4609 |
| 11,478,358 | B2 * | 10/2022 | Miniaci | ................. A61F 2/4014 |
| 12,433,754 | B2 * | 10/2025 | Knox | .................... A61F 2/4014 |
| 2005/0209597 | A1 | 9/2005 | Long et al. | |
| 2008/0249577 | A1 | 10/2008 | Dreyfuss | |
| 2009/0275993 | A1 * | 11/2009 | Phan | ................. A61B 17/8891 |
| | | | | 606/301 |
| 2009/0312766 | A1 | 12/2009 | McMillan et al. | |
| 2010/0161066 | A1 | 6/2010 | Iannotti et al. | |
| 2012/0185059 | A1 * | 7/2012 | Vankoski | .............. A61F 2/4684 |
| | | | | 623/22.24 |
| 2013/0204388 | A1 * | 8/2013 | Meridew | .................. A61F 2/34 |
| | | | | 623/22.36 |
| 2013/0282120 | A1 | 10/2013 | Refai et al. | |
| 2013/0325139 | A1 * | 12/2013 | Steiner | .................. A61F 2/4684 |
| | | | | 623/22.15 |
| 2023/0248539 | A1 * | 8/2023 | Barfield | ............. A61B 17/1746 |
| | | | | 606/99 |

OTHER PUBLICATIONS

Extended European Search Report mailed Oct. 20, 2021, in connection with European Patent Application No. 21170401.0, 10 pgs.

* cited by examiner

TOOL FOR ASSEMBLING AND DISASSEMBLING IMPLANT COMPONENTS

This application is National Stage under 35 U.S.C. 371 of International Patent Application No. PCT/EP2022/060790, filed Apr. 23, 2022, which claims priority to European Patent Application No. 21170401.0, filed Apr. 26, 2021; the disclosures of all of which are incorporated herein by reference in their entirety.

TECHNICAL FIELD

The present disclosure relates to a single tool for both assembling and disassembling implant components to each other, the implant components preferably being implant components of a joint implant, and a method to assemble and disassemble these implant components.

BACKGROUND OF THE INVENTION

Modular implants that are adaptable to a patient have been a success for replacing synovial joints. Such a replacement may become necessary due to arthritis or trauma. The modularity of these implants allows for highly customized joint replacements at reasonable costs.

Nonetheless, the stability and reliability of the connection between implant components of these modular joint implants is crucial for their longevity. In this respect, a common technique for connecting implant components is the use of a tapered connection, which causes a friction fit between components. This type of connection is particularly employed for compressive forces since these forces cause self-locking of this type of connection. An exemplary application of a tapered connection is in a joint implant. A joint implant typically comprises a stem for anchoring the implant within the bone tissue of a bone adjacent to a joint to be replaced. After implantation of the stem, an implant component including a joint surface may be attached to the stem. This attachment is mostly achieved using above-noted tapered connection.

Although these tapered connections have been proven as an effective way to connect implant components to each other, this effectiveness also renders it difficult to adjust the orientation of an implant component or replace such a component by another one, once it has been assembled. In other words, having established the friction fit within the tapered connection, it is necessary for an adjustment or removal to pull the implant components apart from each other along an axial direction of the tapered connection. This is typically achieved using a hammer-like tool that applies an impulse to a component attached to the stem for loosening the tapered connection. As a result, there is a risk of affecting the connection between the implant's stem and the bone tissue of a patient.

The prior art discloses tools and methods for implanting or extracting joint implants, and includes basic devices comprising predominantly of a force transmission structure with a proximal and distal end, handle, elongated retaining elements movable, clamping arms to grab and hold the joint head prosthesis, an actuation mechanism to move the retaining elements between positions, and a contact surface that makes direct and forcible contact with the prosthesis itself, in which the contact surface is the same for both implantation and extraction. See DE 76 01 139 U1 (AESCULAP-WERKE AG) 26 May 1976 and U.S. Pat. No. 5,417,693 A (SOWDEN BJORN K [GB] ET AL) 23 May 1995. The prior art also discloses similar tools for either inserting or removing implants, with the same tools not being used for both and thus a single contact surface. See US 2008/249577 A 1 (DREYFUSS PETER J [US]) 9 Oct. 2008; US 2005/209597 A 1 (LONG JACK F [US] ET AL) 22 Sep. 2005; US 2013/282120 A 1 (REFAI DANIEL [US] ET AL) 24 Oct. 2013.

SUMMARY OF THE INVENTION

Thus, it was an objective to provide an implantation tool for both assembling and disassembling components of a joint implant, in particular components that are attachable to each other by a friction fit and to provide an implantation tool that provides a less direct and more controlled application of impact force, to prevent damage to the implant components. It has also been an objective to provide a tool that allows for an adjustment of the orientation of implant components relative to each other or for a replacement of an implant component after assembly, while preventing an effect on the anchorage of the implant's stem within the bone tissue of a patient.

The present disclosure addresses these objectives by providing a single tool for assembling and disassembling a first implant component and a second implant component. The tool comprises a proximal end, a distal end, and a longitudinal axis. It further comprises an elongated force transmission structure for transmitting a force in a direction along the longitudinal axis. The tool also comprises two elongated retaining elements, wherein each retaining element has a distally facing retaining surface at a proximal end thereof, and an actuation mechanism. The actuation mechanism is operable to move the retaining elements between a standby position and a retaining position, wherein in the retaining position the proximal ends of the retaining elements are closer to each other than in the standby position. The actuation mechanism is characterized by an actuation member with a slanted surface that interacts with distal portions of the retaining elements. The tool also comprises a transmission rod that is rotatable and when rotated after the actuation mechanism has assumed the retaining position interacts with the actuation member to further actuate the actuation mechanism and cause a relative movement of the distally facing retaining surfaces in a distal direction, and said tool including either an assembly adapter, when said tool is used to assemble the implant components, or disassembly adapter, when said tool is used to disassemble the implant components, both adapters configured to be attached to the force transmission structure.

The elongated force transmission structure allows for transmitting a force, in particular caused by an impact force applied to the distal end with a tool (e. g. a hammer) from the distal end to the proximal end of the force transmission structure (i. e. to the first implant component).

In other words, the force transmission structure serves as an intermediate means to transmit and direct an impact force to the first implant component for assembling the first implant component to the second implant component.

Consequently, the elongated force transmission structure is able to protect the first component from direct contact with the impact tool by guiding and directing the impact force to the first component. This prevents the first component from being damaged by the impact force during fixation of the first implant component to the second implant component that may otherwise be caused by a more direct and less controlled application of the impact force.

The retaining elements are for retaining the first implant component during assembly and disassembly of this component to and from the second component. In the standby position, the elongated retaining elements are positioned relative to each other for receiving the first implant component. In particular, the retaining elements are positioned for placing the first implant component on their distally facing retaining surfaces.

Then, the actuation mechanism is configured to move the retaining elements to the retaining position for retaining the first implant component. In the retaining position, the first implant component preferably rests on the distally facing retaining surface and in between the retaining elements. The retaining elements allow for easy handling of the first implant component during assembly and disassembly.

During disassembly, the relative movement of the contact surface of the force transmission structure in relation to the retaining surfaces of the elongated retaining elements may be used for a pull-off movement of the first implant component in relation to the second implant component.

More specifically, the contact surface of the force transmission structure may be in contact with the second implant component. In this state, the further actuation of the actuation mechanism causes relative movement of the distally facing retaining surfaces in a distal direction. As a result, the first implant component also moves distally so that a connection, in particular a friction fit (e. g. by a tapered connection), between the first implant component and the second implant component is released.

Thus, the further actuation of the actuation mechanism facilitates the disassembly of the first and second implant components without affecting the fixation of the implant to the bone tissue of a patient.

The force transmission structure may include a proximally facing contact surface such that said further actuation of the actuation mechanism after assuming the retaining position causes said relative movement of the distally facing retaining surfaces towards the proximally facing contact surface The actuation mechanism is particularly configured to convert a translational movement into a rotational movement of the retaining elements and, when the rotational movement of the retaining elements is blocked, to transfer the translational movement to the retaining elements for causing the relative movement of the distally facing retaining surfaces in relation to the contact surface in a distal direction.

In particular, the translational movement is a translational movement (preferably in the direction of the longitudinal axis) relative to the elongated force transmission structure and its proximally facing contact surface. The actuation mechanism then converts this translational movement to a rotational movement of the retaining elements so that the proximal ends of the retaining elements rotate towards each other for assuming the retaining position.

If this rotational movement of the elongated retaining elements is blocked, the conversion of the translational movement to the rotational movement is stopped. Instead, the translational movement is directly transferred to the elongated retaining elements causing above-noted relative movement to the contact surface in the distal direction. In other words, the translational movement after the rotational movement is blocked corresponds to the further actuation.

Blocking of the rotational movement is particularly caused by the first implant component being present in between the proximal retaining elements and on the distally facing retaining surfaces. As a result, sides of the retaining elements facing each other may get in contact with the first implant component and block the rotational movement.

Nonetheless, any blockage of the rotation may cause the transferal of the translational movement to the retaining elements.

As a result of the actuation mechanism being configured like this, an operator does not have to switch actuation modes since the actuation mechanism is configured as described above.

Preferably, the retaining elements are configured to perform at their proximal ends a gripping motion towards each other to assume the retaining position and a release motion away from each other to assume the standby position.

The gripping motion allows for capturing the first implant component between the elongated retaining elements and the contact surface of the force transmission structure. In the retaining position, the retaining surfaces of the retaining elements prevent a movement of the first implant component in a proximal direction, whereas the contact surface prevents a movement of the first implant component in a distal direction.

Accordingly, the release motion allows to release the first implant component from the tool after assembly or disassembly. This configuration of the retaining elements provides for a secure and easy handling of the first implant component during assembly and disassembly.

The tool may further comprise a base member, wherein the retaining elements are each pivotable about a rotation axis having a fixed position on the base member.

This configuration not only allows for a defined movement of the retaining elements relative to the contact surface of the force transmission structure and the first implant component but also for a predetermined movement of the retaining elements relative to each other.

It is particularly preferred that the actuation member is arranged between distal ends of the retaining elements and includes a distally tapered portion provided with the slanted surface. The distal ends of the retaining elements are in contact with the slanted surface of the distally tapered portion.

This configuration including an actuation member presents a way to guide the distal ends of the retaining elements away from and towards each other. More specifically, a movement of the actuation member in the distal direction relative to the retaining elements causes the distal ends of the retaining elements to move along the slanted surface to a wider section of the actuation member's distally tapered portion, which results in an increased distance between these distal ends and vice versa.

If used in combination with the retaining elements having above-noted rotation axis at the base member, the distal movement of the actuation member causes a movement of the retaining elements towards the retaining position (i. e. towards each other), whereas a proximal movement of the actuation member causes a movement of the retaining elements towards the standby position (i. e. away from each other).

The actuation member of this configuration provides a simple and effective mechanism to transform a longitudinal movement into a rotational movement of the two elongated retaining elements. Further, it allows for adjusting the transmission ratio between the longitudinal and rotational movement making it easier for a user to apply the force needed.

As a result of the above, the actuation member is preferably movable relative to the base member along the longitudinal axis. Guided by the contact of the distal ends of the retaining elements with the slanted surface, a movement of the tapered portion relative to the base member distally pushes the distal ends of the retaining elements away from each other and the proximal ends of the retaining elements towards each other.

Further, the actuation mechanism may further comprise a biasing means, wherein the biasing means is arranged between the base member and the actuation member and biases the base member and the actuation member away from each other along the longitudinal axis.

This preferably results in the retaining elements being biased towards the retaining position. This bias also causes the elongated retaining elements of the tool to always assume a defined position relative to each other and relative to the contact surface of the force transmission structure, in particular since the bias keeps the retaining elements and the base member (in particular the slanted surface) in contact. Thus, there is no slack within the mechanisms of the tool when being handled. Having a bias towards the retaining position also prevents the first implant component from accidentally being released from the tool.

The force transmission structure is preferably arranged between the retaining elements and comprises a transmission rod, the transmission rod may have a through hole extending between the distal and proximal ends of the transmission rod for inserting a fastening tool.

Accordingly, the tool comprising the two elongated retaining elements and the interposed force transmission structure may generally have a symmetrical configuration. This allows for a balanced force application during assembly and disassembly of the first and second implant components.

In particular, the transmission rod extends along the longitudinal axis of the tool. The possibility to insert a fastening tool has the advantage that fastening of the implant components is possible without removing the tool for assembly and disassembly.

Preferably, the transmission rod is in a threaded engagement with the actuation member so that a rotation of the transmission rod relative to the actuation member causes a movement of the actuation member along the longitudinal axis relative to transmission rod and in particular relative to the distal ends of the retaining elements.

Consequently, the transmission rod allows a user to easily rotate the transmission rod (preferably at its distal end), which in turn results in a relative movement between the transmission rod and the actuation member in a longitudinal direction. This relative movement of the actuation member particularly causes the retaining elements to move between the standby position and the retaining position.

The threaded engagement of the transmission rod and the actuation member also has the advantage that it allows for a transmission ratio enabling a precise, easy, and controlled movement of the retaining elements as well as assembly and disassembly of the implant components.

It should be noted that the base member particularly has a central through hole for guiding the transmission rod so that the transmission rod may move along and rotate freely relative to this through hole.

The force transmission structure further preferably comprises an adapter including the contact surface at a proximal end of the adapter and a rod coupling portion at a distal end of the adapter, wherein the rod coupling portion preferably allows for a relative rotation between the adapter and the transmission rod about the longitudinal axis.

Employing an adapter at the proximal end of the transmission rod allows for adaptation of the contact surface to the distal surface of the first implant component. This has the advantage of enhancing the support of the tool. Further, the adapter may prevent a rotation during actuation of the transmission rod by a user.

The enhanced support for the force transmission structure by the adapter at the proximal end of the transmission rod particularly provides a basis for the relative movements from the transmission rod to the actuation member, from the actuation member to the retaining elements and from the retaining elements relative to the first implant component.

The adapter is preferably an assembly adapter for being in contact with the first joint implant component and/or a disassembly adapter for being in contact with the second joint implant component.

When being configured as an assembly adapter, the contact surface of the adapter is preferably in contact with a distal surface, in particular a joint surface, of the first implant component for supporting the tool.

When being configured as a disassembly adapter, the support surface of the adapter is in contact with a distal surface of the second implant component, for example via a through hole through the first implant component, and acts as a support for the tool during disassembly. In this case, the actuation of the tool causes a relative movement between the distally facing retaining surfaces of the retaining elements and the contact surface of the transmission rod (and in particular of the adapter) so that the first implant component and the second implant component move away from each other.

The disclosure further provides an implantation set comprising a tool configured as described above, a first implant component, and a second implant component. The first implant component includes a first connecting portion formed at a proximal end thereof and a through hole with a screw seat for an assembly screw. The through hole extends between the proximal end and a distal end of the first implant component, wherein the first implant component preferably comprises a joint surface at the distal end. The second implant component includes a second connecting portion formed at a distal end thereof and a threaded hole for receiving the assembly screw.

Consequently, this implantation set provides above described advantages resulting in an easy assembly and disassembly of the first and second implant components.

Preferably, the through hole of the first implant component at the screw seat is threaded and even more preferably in the opposite direction in relation to the threaded hole of the second implant component for capturing the assembly screw and serving as a screw seat during fixation. This greatly facilitates handling of the first implant component together with the assembly screw by enabling a pre-assembly of these components.

As a result of this configuration, the assembly screw preferably has an outer thread on the circumferential surface of the assembly screw's head, an outer thread at the opposite end of the assembly screw, and an intermediate section in between, wherein the intermediate section has a smaller diameter than the base diameter of each of these outer threads.

Preferably, one of the first connecting portion and the second connecting portion comprises a male taper and the other one of the first connecting portion and the second connecting portion comprises a female taper.

Such a tapered connection provides for a reliable and releasable connection between implant components. The angle of the tapered connection is also preferably configured to be self-locking.

The present disclosure further discloses a method for preparing a first implant component for assembly to a second implant component using a tool, in particular a tool that is configured as described above. The tool comprises an actuation mechanism, two elongated retaining elements, and a force transmission structure. The method comprises a step of placing the first implant component between proximal ends and onto distally facing retaining surfaces of the retaining elements, wherein the retaining elements are in a standby position for receiving the first implant component. By actuating the actuation mechanism of the tool, the retaining elements assume a retaining position caused by the retaining elements moving closer to each other and by moving the force transmission structure so that a proximally facing contact surface at the proximal end of the force transmission structure abuts the first implant component.

Accordingly, the method allows to securely and easily handle the first implant component prior to entering the implantation site and assembly to the second implant component.

The present disclosure also provides a method for disassembling a first implant component and a second implant component using a tool, in particular a tool configured as described above. The tool includes an actuation mechanism, two elongated retaining elements, and a force transmission structure, and may comprise the step of loosening an assembly screw that fastens the first implant component to the second implant component. The first implant component is placed between proximal ends and onto distally facing retaining surfaces of the retaining elements, wherein the retaining elements are in a standby position for receiving the first implant component. Then, the actuation mechanism of the tool is actuated for assuming a retaining position by moving the retaining elements closer to each other and by moving the force transmission structure proximally to abut the head of the assembly screw with a proximally facing contact surface at the proximal end of the force transmission structure. After the retaining elements assumed the retaining position, actuating the actuation mechanism continues for moving the retaining elements distally in order to pull the first implant component away from the second implant component.

This method is particularly directed at a connection between implant components that is based on a friction fit.

Disassembling the first implant component and the second implant component advantageously releases the two implant components from each other in a controlled and defined way without exerting an impact force on the patient that may adversely affect the interface formed between bone tissue and the implant. In other words, this method achieves disassembly of the implant components without the need for an impact tool such as a hammer to release the implant components from each other.

In this way, surgery is performed more gently, which supports a faster recovery of the patient. Also, the implant may be more easily adapted to an anatomic environment (e. g. properties of tendons and muscles) that has changed over time due to aging of the patient. If needed, the replacement of worn implant components, in particular joint surfaces, is facilitated, which significantly increases the lifetime of the implant.

DETAILED DESCRIPTION OF PREFERRED EMBODIMENTS

In the following, exemplary configurations of tools for assembling and disassembling implant components according to the present disclosure are described under reference to the attached drawings that illustrate preferred embodiments of these tools.

Figure 1:
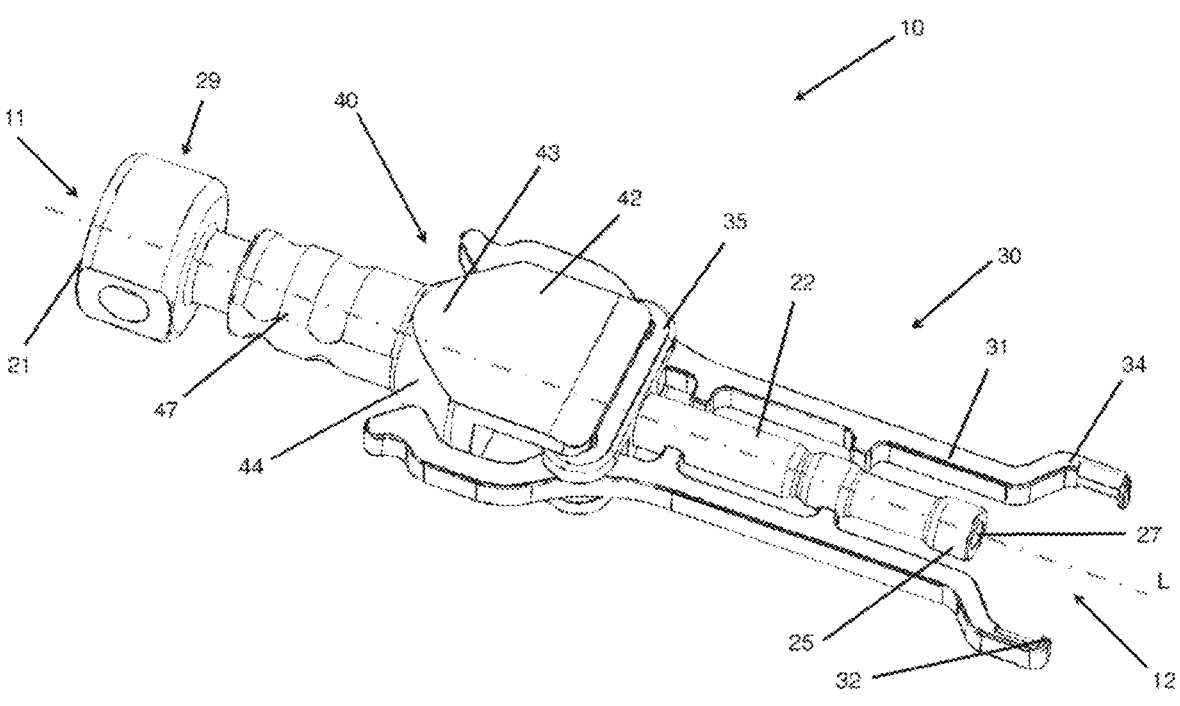
FIG. 1 is a three-dimensional view of a tool for assembling and disassembling implant components according to the present disclosure.

FIG. 1 illustrates an exemplary embodiment of the tool 10 for assembling and disassembling implant components. The tool 10 may, for example, be used for an implantation or revision of an implant component. However, the skilled person appreciates that the assembly and disassembly of implant components may also take place outside of a patient's body.

The tool 10 has a distal end 11 and a proximal end 12 at opposite ends of the tool's longitudinal axis L. When being used during an implantation or revision of an implant component, the distal end 11 is directed away from whereas the proximal end 12 is directed towards the patient's body.

Figure 2:
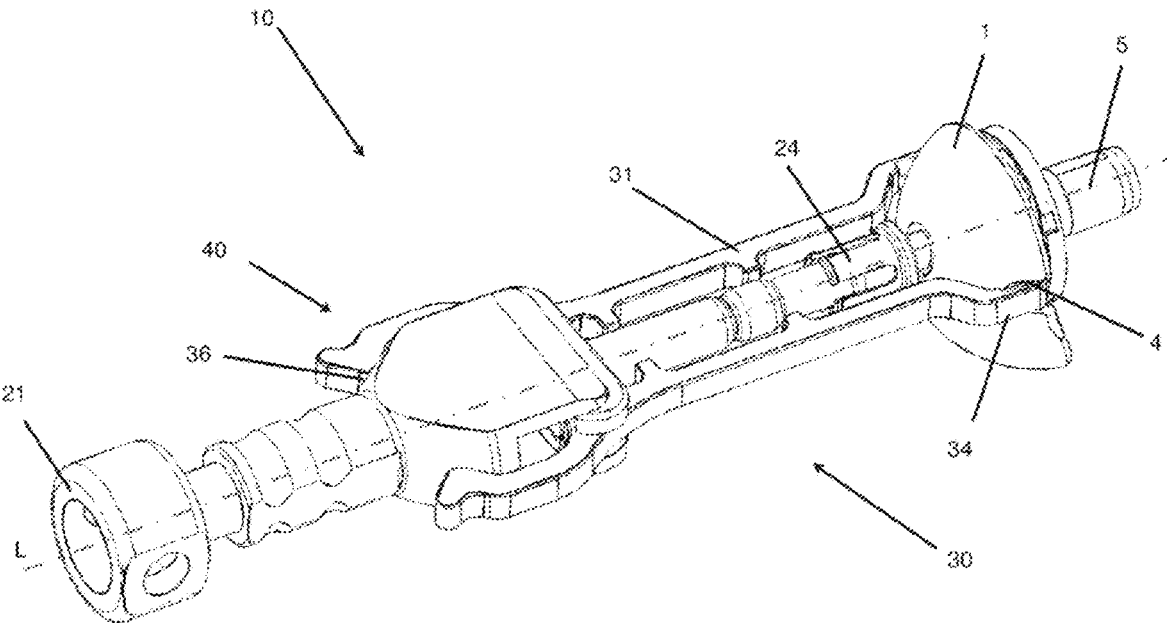
FIG. 2 is a three-dimensional view of the tool in engagement with a first and second component of a joint implant during disassembly.

Further, the tool 10 includes a force transmission structure 20 for transmitting an assembly force (in particular a compressive force or an impact force for causing a friction fit) along the longitudinal axis L of the tool 10, a retaining mechanism 30 for retaining a first implant component 1 (see FIG. 2), and an actuation mechanism 40 for actuating the retaining mechanism 30.

The force transmission structure 20 extends from the distal end 11 towards the proximal end 12 of the tool 10 and includes a transmission rod 22 for transferring a force along the longitudinal axis between the proximal and distal ends of the force transmission structure 20. The transmission rod 22 is preferably integrally formed.

At the distal end 11, the force transmission structure 20 and in particular the transmission rod 22 may have an impact face 21 for exerting an impact force to the force transmission structure 20 that is then transmitted to the proximal end of this structure, where it can be applied to an implant component. An impact force is typically applied during assembly of a first implant component 1 and a second implant component 5 for fixing these implant components to each other (see FIGS. 3 to 5).

At the proximal end, the transmission rod 22 may have a contact surface (not shown in this embodiment) for being in contact with an implant component 1 or 5 during assembly or disassembly.

Nonetheless, the proximal end preferably includes a rod coupling portion 25. This rod coupling portion 25 serves for mounting an assembly adapter 23 (see FIGS. 3 to 5, 8 and 9) or a disassembly adapter 24 (see FIGS. 2, 6, and 7).

The adapters 23 and 24 and the rod coupling portion 25 are preferably configured for an assembly using a snap-fit. Nonetheless, this skilled person will appreciate that other means may be used, such as a friction fit or an insertion of one of the rod coupling portion and the adapter into the other one of the rod coupling portion and the adapter, as long as a compressive force can be applied via the transmission rod 22 and either one of the adapters 23, 24.

Further, the connection between the transmission rod 22 and the adapters 23, 24 preferably allows for a relative rotation about the longitudinal axis L.

Figures 3, 4, 5:
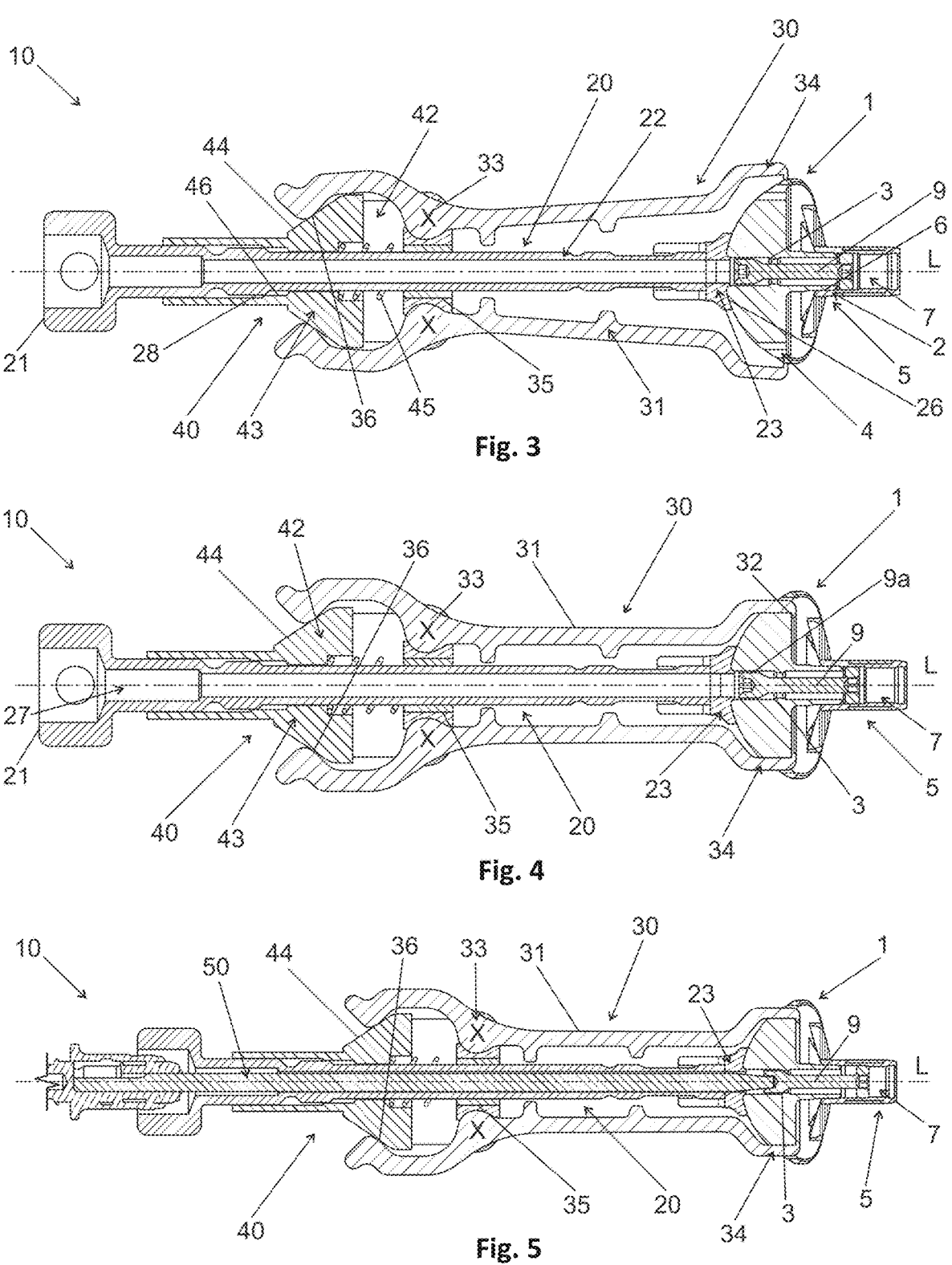
FIG. 3 is a longitudinal cross-section illustrating the tool in a state during engagement with a first joint implant component.
FIG. 4 is a longitudinal cross-section illustrating the tool in engagement with the first joint implant component.
FIG. 5 is a longitudinal cross-section illustrating the tool in engagement with the first joint implant component while a fastening tool is inserted for securing the first joint implant component to another, second joint implant component via a fastening element.

Extending from its proximal to its distal end, the transmission rod 22 may also comprise a through hole 27 for a fastening tool 50 (see FIG. 5). The fastening tool 50 may, for example, be used for fastening and unfastening the first implant component 1 and the second implant component 5 via an assembly screw 9 for preventing an unintended loosening of these components (i. e. to secure them to each other).

Turning to the interaction of the retaining mechanism 30 and the actuation mechanism 40, the actuation mechanism 40 is for actuating the retaining mechanism 30. By actuating the retaining mechanism 30, the retaining elements 31 are able to retain and to release a first implant component 1.

As shown in the figures, the retaining mechanism 30 comprises two retaining elements 31. However, the retaining mechanism 30 may also comprise more than two retaining elements 31, such as three, four or five retaining elements 31.

The retaining elements 31 are elongated and are arranged along the longitudinal axis L with the transmission rod 22 located in between.

At their proximal ends, the retaining elements 31 are configured to retain an implant component. An implant component 1 may be retained between proximal retaining sections 34 of the retaining elements 31. These proximal retaining sections 34 may enter corresponding retaining recesses 4 of the implant component 1 so as to retain the implant component 1 between these proximal retaining sections 34. The engagement of the proximal retaining sections 34 also prevents a rotation of the implant component 1 about the longitudinal axis L relative to the tool 10.

The elongated retaining elements 31 include distally facing retaining surfaces 32 at their proximal ends. In a retaining position, these distally facing retaining surfaces 32 prevent a proximal movement of the implant component 1 in relation to the tool 10.

As illustrated in the figures, the proximal retaining sections 34 of the retaining elements 31 may also be formed to extend at a distance along a part of (e. g. the distally facing) outer contour of a retained implant component 1 (first implant component). This configuration limits a movement of the implant component 1 in a distal direction, which particularly helps when mounting the first implant component 1 to the tool 10.

However, in the retaining position, it is the contact surface 26 of the elongated force transmission structure 20 that prevents a movement of the implant component 1 in the distal direction. More specifically, the implant component 1 is retained in the proximal-distal direction between the distally facing retaining surfaces 32 and the proximally facing contact surface 26.

Between their proximal and distal ends, the retaining elements 31 are pivotably supported about rotation axes 33 (see for example FIG. 3) by a base member 35. Preferably, the rotation axes 33 are located more distally along the retaining elements 31. As illustrated in the figures, the rotation axes 33 particularly extend perpendicular to and are arranged symmetrically and at a distance to the longitudinal axis L of the tool 10. However, different configurations are also envisaged such as using one rotation axis 33 for the retaining elements 31.

Each of the retaining elements 31 includes at its distal end a gliding surface 36 facing in a direction towards the longitudinal axis L. As will be explained in the following, these gliding surfaces 36 interact with the actuation mechanism 40 in order to move (in particular pivot about the rotations axes 33) the retaining elements between a standby position and a retaining position in order to mount and unmount an implant component 1 at the proximal retaining section 34 of the retaining elements 31.

Turning to the actuation mechanism 40, the actuation mechanism 40 comprises an actuation member 42. The actuation member 42 includes a distally tapered portion 43 formed with a slanted actuation surface 44 to be in contact with the gliding surface 36 of each retaining element 31. In the exemplary embodiment of the figures, the slanted actuation surface 44 comprises two slanted actuation surfaces on opposite sides relative to the longitudinal axis L for interacting with the gliding surfaces 36 of the retaining elements 31, respectively. In other words, the slanted actuation surfaces 44 are arranged at an angle to the longitudinal axis L and particularly face in a distal direction.

As a result of this configuration, a movement of the actuation member 42 and, thus, its slanted actuation surfaces 44 along the longitudinal axis L and relative to the base member 35 of the retaining mechanism 30 causes a movement of the distal ends with the gliding surfaces 36 of the retaining elements 31 in a perpendicular direction to the longitudinal axis L while rotating about the rotation axes 33.

More specifically, a movement of the actuation member 42 in the distal direction causes the distal ends of the retaining elements 31 to move away from each other due to the contact of the gliding surfaces 36 with the slanted actuation surfaces 44 of the actuation member's distally tapered portion 43 (cf. FIGS. 3 to 4).

Due to the pivotal support of the retaining elements 31 at the base member 35, this movement of the distal ends of the retaining elements 31 causes the proximal retaining sections 34 to move towards each other. In other words, this movement causes the proximal retaining sections 34 to switch between the standby position and the retaining position.

Accordingly, a movement of the actuation member 42 in the proximal direction allows for the proximal retaining sections 34 to move from the retaining position to the standby position and to release the implant component 1 (cf. FIGS. 4 to 3).

As illustrated in FIGS. 3 to 5, the actuation mechanism 40 may further include a biasing means 45 (e.g. a spring). The biasing means 45 is arranged and acts between the base member 35 and the actuation member 42. It preferably biases the base member 35 and the actuation member 42 away from each other along the longitudinal axis L and, thus, towards the retaining position of the retaining elements 31. This has the advantage that the tool 10 does not move unintentionally between the retaining position and the standby position.

An operator preferably actuates the actuation mechanism 40 via a rotation of the transmission rod 22. More specifically, the transmission rod 22 preferably comprises an actuation thread 28 that engages an actuation thread 46 of the actuation member 42. Consequently, turning the transmission rod 22 about the longitudinal axis L while holding the actuation member 42 in position (for example using a grip portion 47 of the actuation member 42) causes a relative translational movement between the actuation member 42 and the transmission rod 22 along the longitudinal axis L. For operating the transmission rod 22, the distal end of the transmission rod 22 may include an operating section 29 such as a knob and/or a recess/through hole for inserting a lever arm.

The operation of the tool 10 for assembling and disassembling the implant components 1 and 5 will now be described under reference to FIGS. 3 to 9.

FIGS. 3 to 5, 8, and 9 illustrate the process of assembling a first implant component 1 to a second implant component 5 using a tool 10 according to the present disclosure.

FIG. 3 depicts the tool 10 in a standby position for receiving a first implant component 1. In the standby position, the proximal retaining sections 34 of the retaining elements 31 are at a distance from each other perpendicular to the longitudinal axis L. In this state, the first implant component can preferably pass by the distal ends of the retaining elements 31 in a distal direction until being in contact with the contact surface 26 of the force transmission structure 20.

Although shown in FIG. 3, the second implant component 5 is not necessarily present when mounting the first implant component 1 to the tool 10 in the standby position but may be added later during an assembly of the first implant component 1 to the second implant component 5 (e. g. the second implant component 5 may already be implanted).

In the exemplary embodiment of FIGS. 3 to 5, the contact surface 26 is formed at the proximal end of an assembly adapter 23. As described above, the assembly adapter 23 is attached to the proximal end of the transmission rod 22 and is in particular rotatable relative to the transmission rod 22 about the longitudinal axis L. The contact surface 26 is preferably formed so as to correspond to the distally facing surface of the first implant component 1 the contact surface 26 abuts to.

The assembly adapter 23 shown in FIGS. 3 to 5 is particularly adapted to a distally facing surface of the implant component 1 (e. g. joint surface) that is symmetrical about the longitudinal axis L in the contact area with the contact surface 26.

Figures 6, 7, 8, 9:
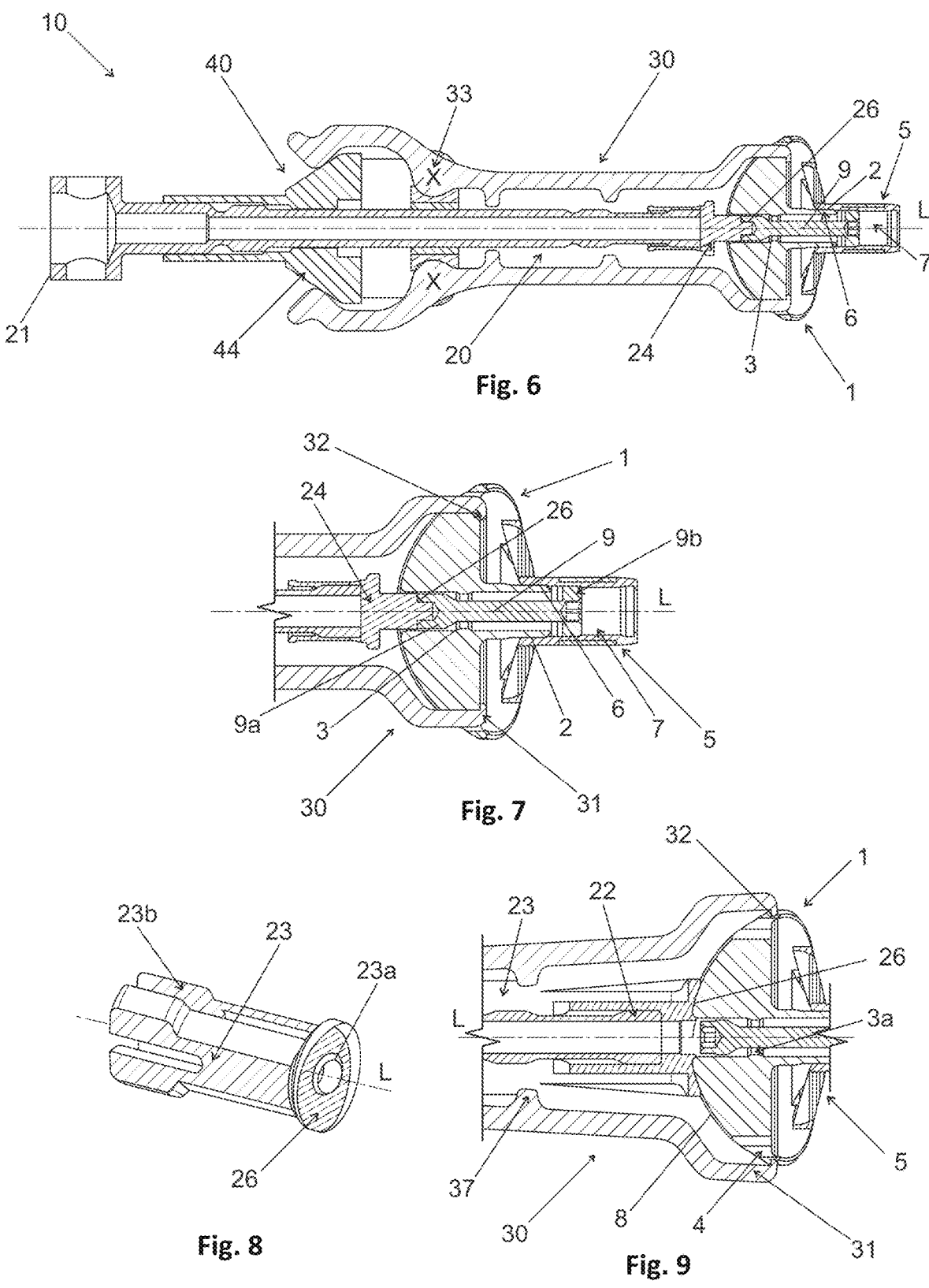
FIG. 6 is a longitudinal cross-section illustrating the tool in engagement with the joint implant components for pulling the first joint implant component and the second joint implant component apart from each other to release a friction fit connection between these implant components.
FIG. 7 is an enlarged section of the cross-section shown in FIG. 6.
FIG. 8 is a three-dimensional view of an adapter for assembling a first joint implant component with an asymmetrical joint surface to a second joint implant component.
FIG. 9 is a longitudinal cross-section illustrating the adapter of FIG. 8 assembled to the implantation tool and during engagement with a first implant component.

In contrast, the assembly adapter 23 shown in FIGS. 8 and 9 has a contact surface 26 configured to be in contact with a distally facing surface of the first implant component 1 that is asymmetrical in relation to the longitudinal axis L. In this case, the assembly adapter 23 preferably comprises a collar 23a that fits into the aperture of the through hole 3 of the first implant component 1. The fit of the collar 23a is adapted to prevent the adapter 23 from slipping sideways relative to the longitudinal axis due to the asymmetrical surface 8 of the first implant component 1.

In this respect, the adapter 23 and the retaining elements 31 may also comprise an interacting nose-recess configuration for preventing the adapter 23 to rotate about the longitudinal axis L, at least in the retaining position and in particular in case of an asymmetrical surface as described above.

FIG. 9 shows an example of such a nose-recess configuration. Here, the adapter 23 includes a recess 23b and the retaining element 31 includes a nose 37. As illustrated in FIG. 9 with adapter 23 in cross-section, the nose 37 protrudes into the recess 23b (here formed as a longitudinal groove) when the adapter 23 is assembled to the proximal end of the transmission rod 22. In this example, the nose 37 is interacting with the recess 23b in both the standby position and the retaining position.

As shown in the figures, the implant components 1, 5 to be assembled are preferably joint implant components. Thus, the distally facing surface 8 of the first implant component 1 is preferably the joint surface of the joint implant. In particular in this case, it is advantageous to adapt the contact surface 26 of the assembly adapter 23 in order to enhance the distribution of loads, in particular impact loads, during assembly of the first implant component 1 to the second implant component 5.

Likewise, the relative rotation that is allowed between the transmission rod 22 and the assembly adapter 23 prevents a relative rotation between the contact surface 26 of the assembly adapter 23 and the joint surface of the first implant component 1. As described above, such a rotation may also be prevented by a nose-recess configuration between the adapter 23 and the retaining elements 31.

Preferably, the assembly adapter 23 is made of a polymer for preventing the distally facing surface 8 of the first implant component 1 to be damaged. An assembly adapter 23 made of a polymer also has the advantage that a relative rotation between the assembly adapter 23 and the first implant component 1 is unlikely to have an adverse effect on the distally facing surface of the first implant component 1.

Once the first implant component 1 is moved distally beyond the proximal ends of the retaining elements 31 and abuts the contact surface 26 of the assembly adapter 23, a user may rotate the transmission rod 22 about the longitudinal axis L in order to cause a movement of the actuation member 42 in the distal direction relative to the transmission rod 22 due to the threaded engagement of the actuation threads 28, 46.

As described above, this in turn results in the gliding surfaces 36 of the retaining elements 31 gliding proximally along the slanted actuation surfaces 44 of the actuation members distally tapered portion 43 so that the distal ends of the retaining elements 31 move away from each other in a direction perpendicular to the longitudinal axis L. Accordingly, the proximal ends of the a retaining elements 31 move towards each other due to the pivotal support of the retaining elements 31 about the rotation axes 33 of the base member 35. This movement of the retaining elements' proximal ends makes the proximal retaining sections 34 close around a section of the first implant component 1.

At the end of this movement, the distally facing retaining surfaces 32 of the retaining elements 31 are facing and support a proximally facing surface of the first implant component 1, and the tool 10 has assumed its retaining position (see FIG. 4). As shown in FIG. 4, the first implant component 1 is now retained between the distally facing retaining surfaces 32 of the retaining elements 31 and the proximally facing contact surface 26 of the assembly adapter 23. The clamping force exerted between the distally facing retaining surfaces 32 and the contact surface 26 is adjusted by turning the transmission rod 22.

Consequently, the tool 10 is configured to move from the standby position to the retaining position so that the proximal retaining sections 34 of the retaining elements 31 enclose the first implant component 1 before the contact surface 26 and the distally facing retaining surfaces 32 exert a clamping force to the first implant component 1.

In particular the threaded engagement between the transmission rod 22 and the actuation member 42, the interaction between the slanted actuation surfaces 44 of the distally tapered portion 43 and the gliding surfaces 36 of the retaining elements 31, the location of the rotation axes 33 along the retaining elements 31 and/or the distance between the contact surface 26 and the distally facing retaining surfaces 32 along the longitudinal axis L may be configured to enhance this functionality of the tool 10 by adjusting the transmission ratios between these components of the tool 10.

As already mentioned above, the first implant component 1 may also comprise a retaining recess 4 for receiving a proximal retaining section 34 of a retaining element 31. This prevents an unintended rotation of the first implant component 1 relative to the tool 10.

Further, releasing the first implant component 1 from the tool 10 may be achieved by actuating the tool 10 in the reverse direction.

The first implant component 1 includes a first connecting portion 2 and the second implant component 5 includes a corresponding second connecting portion 6 for attaching the first implant component 1 and the second implant component 5 to each other. Preferably, the connecting portions 2 and 6 are configured as a tapered connection, in particular a self-locking tapered connection.

In particular in case of a tapered connection, the first implant component 1 and the second implant component 5 are assembled to each other using an impact force applied to the impact face 21 of the force transmission structure 20 and transmitted via the transmission rod 22 and the assembly adapter 23 to the first implant component 1. As a result, the first implant component 1 moves towards the second implant component 5.

After mounting the first implant component 1 to the second implant component 5, the implant components are preferably secured to each other using an assembly screw 9. As shown in FIG. 5, the assembly screw 9 is preferably fastened using a fastening tool 50 that is inserted into the through hole 27 of the force transmission structure 20 (i.e. the transmission rod 22 and the assembly adapter 23) and engages the head of the assembly screw 9. Thus, the implant components 1, 5 may be secured to each other more easily due to being guided by the tool 10.

For securing the first implant component 1 to the second implant component 5 by an assembly screw 9, the first implant component 1 comprises a through hole 3. The through hole 3 includes a screw seat 3a for engaging the head 9a of the assembly screw 9.

At a proximal portion 9b, the assembly screw 9 includes an outer thread for engaging and inner thread of a threaded hole 7 included in the second implant component 5. The through hole 3 as well as the threaded hole 7 (e. g. a through hole with a threaded portion) are extending through the respective implant component 2, 5 in a proximal-distal direction (in particular along the longitudinal axis L).

For securing the first and second implant components 1, 5, the assembly screw 9 is fastened by its threaded engagement with the threaded hole 7 of the second implant component 5 until the head 9a of the assembly screw 9 interacts with the screw seat 3a of the through hole 3 of the first implant component 1. This secures the first implant component 1 to the second implant component 5 against unintended loosening.

Preferably, the screw seat 3a is formed by and at a distal end of an inner thread within the through hole 3 of the first implant component 1. The inner thread of the through hole 3 is even more preferably formed in an opposite direction in relation to the thread of the threaded hole 7 of the second implant component 5 (i. e. right hand thread and left hand thread or vice versa).

As described above, the head 9a of the assembly screw 9 may have an outer thread for engaging the inner thread of the through hole 3. Accordingly, the assembly screw 9 may be pre-assembled to the first implant 1 component by screwing the assembly screw 9 past the inner thread of the through hole 3.

Since the inner thread of the through hole 3 is formed in the opposite direction relative to the threaded hole 7 and the outer thread at the proximal end of the assembly screw 9, the head of the assembly screw 9 does not engage the inner thread of the through hole 3 so that the inner thread of the through hole 3 acts as a screw seat 3a.

As will be explained in the following under reference to FIGS. 6 and 7, the assembly screw 9 further allows for an easy disassembly of the first and second implant components 1 and 5.

Before disassembly, the assembly screw 9 is unfastened, preferably until it disengages the threaded hole 7 of the second implant component 5. In this state, the assembly screw 9 rests proximally in relation to the second connecting portion at the distal end of the threaded hole 7 (i. e. the threaded hole 7 acts as a screw seat for the threaded tip portion 9b of the assembly screw 9).

For disassembly, the tool 10 engages the first implant component 1 as described above by a user turning the transmission rod 22 of the force transmission structure 20. In contrast to an assembly using an assembly adapter 23, for disassembly a disassembly adapter 24 is employed.

As illustrated in FIG. 6, the disassembly adapter 24 is also mounted to the proximal end of the transmission rod 22. In contrast to the assembly adapter 23 described above, the contact surface 26 of the disassembly adapter 24 does not interact with the first implant component but instead with the head 9a of the assembly screw 9 and via the proximal portion 9b of the assembly screw 9 with the second implant component 5.

In particular, the contact surface 26 of the disassembly adapter 24 abuts the head of the assembly screw 9 that has previously been unscrewed from the threaded hole 7 of the second implant component 5. Thus, in the retaining position, the first implant component 1 is clamped between the distally facing retaining surfaces 32 of the retaining elements 31 and the assembly screw 9. As a result, the clamping force acts on the first connecting portion 2 of the first implant component 1 and the second connecting portion 6 of the second implant component 5 as a force separating these two implant components.

This interaction is used for disassembling the first implant component 1 from the second implant component 5, i.e. for releasing the connection between the first connecting portion 2 and the second connecting portion 6. This is achieved by actuating (i. e. turning) the transmission rod 22 further after the retaining position has been assumed so that the actuation member 42 moves further distally.

As can be appreciated from FIG. 6, the further movement of the actuation member 42 in the distal direction causes the retaining elements 31 to move in the same direction. More specifically, since the proximal retaining sections 34 of the retaining elements 31 are prevented from moving further towards each other due to the first implant component 1 being interposed between the proximal retaining sections 34, the gliding surfaces 36 are not able to continue their movement along the slanted actuation surface 44 of the actuation member's distally tapered portion 43. Consequently, the retaining elements 31 and the base member 35 start moving distally relative to the transmission rod 22. For this relative movement, the through hole in the base member 35 is configured to let the transmission rod 22 move and rotate freely, as has been previously described above.

This movement of the retaining elements 31 in a distal direction results in a pull-off motion of the first implant component 1 caused by the contact of the first implant component with the distally facing retaining surfaces 32. Accordingly, disassembly of the first implant component 1 from the second implant component 5 is caused by a defined and controlled movement instead of an impact force.

It should be noted, that the tool 10 illustrated in FIG. 6 may also include a biasing means 45 that has also been described in more detail above.

REFERENCE SIGNS 1 first implant component
2 first connecting portion
3 through hole
3a screw seat (in particular formed by a thread)
4 retaining recess
5 second implant component
6 second connecting portion
7 threaded hole
8 distally facing surface
9 assembly screw
9a head
9b proximal portion
10 tool
11 distal end of the tool
12 proximal end of the tool
20 force transmission structure
21 impact face
22 transmission rod
23 assembly adapter
23a collar
23b recess
24 disassembly adapter
25 rod coupling portion
26 contact surface
27 through hole for fastening tool
28 actuation thread
29 operating section
30 retaining mechanism
31 retaining element
32 distally facing retaining surface
33 rotation axis
34 proximal retaining section
35 base member
36 gliding surface
37 nose
40 actuation mechanism
42 actuation member
43 distally tapered portion
44 slanted actuation surface
45 biasing means
46 actuation thread
47 grip portion 50 fastening tool
L longitudinal axis
The invention claimed is:

1. A tool for assembling and disassembling a first implant component and a second implant component, the tool comprising:
   a proximal end, a distal end, and a longitudinal axis;
   an elongated force transmission structure for transmitting a force in a direction along the longitudinal axis;
   two elongated retaining elements, each retaining element having a distally facing retaining surface at a proximal end thereof;
   an actuation mechanism, wherein the actuation mechanism is operable to move the retaining elements between a standby position and a retaining position, wherein in the retaining position the proximal ends of the retaining elements are closer to each other than in the standby position; and
      said actuation mechanism wherein an actuation member with a slanted surface that interacts with distal portions of the retaining elements
      said elongated force transmission structure including a transmission rod that is rotatable and when rotated after the actuation mechanism has assumed the retaining position interacts with the actuation member to further actuate the actuation mechanism and cause a relative movement of the distally facing retaining surfaces in a distal direction; and
      said tool including either an assembly adapter, when said tool is used to assemble the implant components, or a disassembly adapter, when said tool is used to disassemble the implant components, both adapters configured to be attached to the force transmission structure.

2. The tool of claim 1, wherein the force transmission structure includes a proximally facing contact surface, wherein said further actuation of the actuation mechanism after assuming the retaining position causes said relative movement of the distally facing retaining surfaces towards the proximally facing contact surface.

3. The tool of claim 1, wherein the retaining elements are configured to perform at their proximal ends a gripping motion towards each other to assume the retaining position and a release motion away from each other to assume the standby position.

4. The tool of claim 1, further comprising a base member, wherein the retaining elements are each pivotable about a rotation axis having a fixed position in relation to the base member.

5. The tool of claim 4, wherein the actuation mechanism further comprises a biasing means, wherein the biasing means is arranged between the base member and the actuation member and biases the base member and the actuation member away from each other along the longitudinal axis.

6. The tool of claim 1, wherein the actuation member is arranged between the distal ends of the retaining elements and includes a distally tapered portion provided with the slanted surface, wherein the distal ends of the retaining elements are in contact with the slanted surface of the distally tapered portion.

7. The tool of claim 6, further comprising a base member, wherein the actuation member is movable relative to the base member along the longitudinal axis, wherein guided by contact of the distal ends of the retaining elements with the slanted surface, a movement of the tapered portion relative to the base member in a distal direction is configured to cause the distal ends of the retaining elements to move away from each other and configured to cause the proximal ends of the retaining elements to move towards each other.

8. The tool of claim 1, wherein the transmission rod is arranged between the retaining elements and the transmission rod has a through hole extending between the distal and proximal ends of the transmission rod for inserting a fastening tool.

9. The tool of claim 8, wherein the transmission rod is in a threaded engagement with the actuation member so that a rotation of the transmission rod relative to the actuation member causes a movement of the actuation member along the longitudinal axis relative to the distal ends of the retaining elements.

10. The tool of claim 8, wherein the force transmission structure includes a proximally facing contact surface.

11. The tool of claim 10, wherein the force transmission structure further comprises an adapter comprising the contact surface at a proximal end of the adapter and a rod coupling portion at a distal end of the adapter, wherein the adapter is an assembly adapter for being in contact with the first implant component and/or a disassembly adapter for being in contact with assembly screw of the second implant component, and wherein the rod coupling portion allows for a relative rotation between the adapter and the transmission rod about the longitudinal axis.

12. A method for preparing a first implant component for assembly to a second implant component using the tool of claim 1, wherein the tool comprises an actuation mechanism, two elongated retaining elements, a force transmission structure, and an assembly adapter, wherein the method comprises the steps of:

placing the first implant component between proximal ends and onto distally facing retaining surfaces of the retaining elements, wherein the retaining elements are in a standby position for receiving the first implant component; and actuating the actuation mechanism of the tool for assuming a retaining position by moving the retaining elements closer to each other and by moving the force transmission structure to abut the first implant component with a proximally facing contact surface at the proximal end of the force transmission structure.

13. A method for disassembling a first implant component and a second implant component using the tool of claim 1, wherein the tool comprises an actuation mechanism, two elongated retaining elements, and a force transmission structure, and a disassembly adapter, wherein the method comprises the steps of:

loosening an assembly screw that fastens the first implant component to the second implant component;

placing the first implant component between proximal ends and onto distally facing retaining surfaces of the retaining elements, wherein the retaining elements are in a standby position for receiving the first implant component;

actuating the actuation mechanism of the tool for assuming a retaining position by moving the retaining elements closer to each other and by moving the force transmission structure proximally to abut a head of the assembly screw with a proximally facing contact surface at the proximal end of the force transmission structure; and after the retaining elements assumed the retaining position, continuing with actuating the actuation mechanism for moving the retaining elements distally in order to pull the first implant component away from the second implant component.

* * * * *